(12) United States Patent
Powell et al.

(10) Patent No.: US 6,972,346 B2
(45) Date of Patent: Dec. 6, 2005

(54) SOLID ACID CATALYZED REACTIVE STRIPPING OF IMPURITIES FORMED DURING THE PRODUCTION OF 1, 3-PROPANEDIOL

(75) Inventors: Joseph Broun Powell, Houston, TX (US); Paul Richard Weider, Houston, TX (US); Glenn Charles Komplin, Houston, TX (US)

(73) Assignee: Shell Oil Company, Houston, TX (US)

( * ) Notice: Subject to any disclaimer, the term of this patent is extended or adjusted under 35 U.S.C. 154(b) by 222 days.

(21) Appl. No.: 10/676,796

(22) Filed: Oct. 1, 2003

(65) Prior Publication Data

US 2004/0087819 A1 May 6, 2004

Related U.S. Application Data

(60) Provisional application No. 60/423,097, filed on Nov. 1, 2002.

(51) Int. Cl.[7] .................... C07C 31/18; C07C 31/20; C07C 29/74; C07C 27/26; C07C 27/28
(52) U.S. Cl. .................. 568/868; 568/862; 568/866; 568/867; 568/872
(58) Field of Search .................. 568/862, 866, 568/867, 868, 872

(56) References Cited

U.S. PATENT DOCUMENTS

| | | | |
|---|---|---|---|
| 5,008,473 A | 4/1991 | Breitkopf et al. | 568/868 |
| 5,527,973 A | 6/1996 | Kelsey | 568/862 |
| 5,786,524 A | 7/1998 | Powell et al. | 568/862 |
| 6,235,948 B1 | 5/2001 | Sunkara et al. | 568/868 |
| 6,297,408 B1 * | 10/2001 | Haas et al. | 568/862 |

FOREIGN PATENT DOCUMENTS

| | | | | |
|---|---|---|---|---|
| WO | WO 98/49216 | 11/1998 | | C08G/63/78 |
| WO | WO 00/10953 | 3/2000 | | C07C/29/80 |

* cited by examiner

*Primary Examiner*—Elvis O. Price

(57) ABSTRACT

A process for producing 1,3-propanediol comprising the steps of: a) forming an aqueous solution of 3-hydroxypropanal, b) hydrogenating the 3-hydroxypropanal to form a first crude 1,3-propanediol mixture comprising 1,3-propanediol, water, and MW 132 cyclic acetal, c) distilling the first crude 1,3-propanediol mixture to remove water and low boiling impurities and form a second crude 1,3-propanediol mixture, d) contacting the second crude 1,3-propanediol mixture with a solid acid purifier at a temperature of from about 50 to about 250° C. to convert the MW 132 cyclic acetal to more volatile cyclic acetals, and e) separating the more volatile cyclic acetals from the 1,3-propanediol by distillation or gas stripping.

12 Claims, No Drawings

SOLID ACID CATALYZED REACTIVE STRIPPING OF IMPURITIES FORMED DURING THE PRODUCTION OF 1, 3-PROPANEDIOL

This application claims the benefit of U.S. Provisional Application No. 60/423,097 filed Nov. 1, 2002, the entire disclosure of which is hereby incorporated by reference.

FIELD OF THE INVENTION

This invention relates to a process for the production of 1,3-propanediol (PDO) wherein an aqueous solution of 3-hydroxypropanal (HPA) is formed, and the HPA is hydrogenated to produce a PDO mixture that is distilled to produce purified PDO.

BACKGROUND OF THE INVENTION

Several companies have developed technology for the manufacture of PDO starting with ethylene oxide as the main raw material. The ethylene oxide is reacted with synthesis gas (syngas), a mixture of carbon monoxide and hydrogen, which may be obtained by steam reforming of natural gas or partial oxidation of hydrocarbons. The idealized reaction of ethylene oxide (EO) with syngas to yield PDO is shown below:

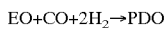

$$EO + CO + 2H_2 \rightarrow PDO$$

U.S. Pat. Nos. 4,873,378, 4,873,379, and 5,053,562 from Hoechst Celanese describe a single step reaction using 2:1 (molar) syngas at 110 to 120° C. and about 1000 psig (6900 kPa) to give 65 to 78 mole percent yield of PDO and precursors thereof. The catalyst system used consisted of rhodium, various phosphines, and various acids and water as promoters.

U.S. Pat. Nos. 5,030,766 and 5,210,318 to Union Carbide describe the reaction of EO with syngas in the presence of rhodium-containing catalysts. At 110° C. and 1000 psig (6900 kPa) of 2:1 molar syngas, a selectivity of up to 47 mole percent was achieved but the combined rate of formation of PDO and 3-hydroxy propanal was quite low at 0.05 to 0.07 moles per liter per hour. Better results were achieved by increasing the ratio of phosphoric acid promoter to rhodium catalyst.

U.S. Pat. Nos. 5,256,827, 5,304,686, and 5,304,691 to Shell Oil described PDO production from EO and syngas utilizing tertiary phosphine-complexed cobalt carbonyl catalysts. Reaction conditions of 90 to 105° C. and 1400 to 1500 psig (9650 to 10,340 kPa) of syngas (1:1 molar ratio) for three hours produced selectivities in the range of 85 to 90 mole percent and the EO conversion was in the range of 21 to 34 percent. Later work reported increased selectivity and EO conversion.

MW 132 acetal of PDO forms as an undesired byproduct of the hydroformylation and hydrogenation reactions. MW 132 is difficult to separate from PDO by simple distillation because it exhibits a volatility similar to PDO. Its formation lowers the overall recovery of PDO as well as its purity. Therefore, it would be highly advantageous to have a process wherein the MW 132 acetal could be chemically reacted to other materials which are more easily separated from PDO. The present invention provides such a chemical method.

SUMMARY OF THE INVENTION

A process for producing 1,3-propanediol comprising the steps of:
a) forming an aqueous solution of 3-hydroxypropanal,
b) hydrogenating the 3-hydroxypropanal to form a first crude 1,3-propanediol mixture comprising 1,3-propanediol, water, and MW 132 cyclic acetal,
c) distilling the first crude 1,3-propanediol mixture to remove water and low boiling impurities and form a second crude 1,3-propanediol mixture,
d) contacting the second crude 1,3-propanediol mixture with an acid form cationic exchange resin at a temperature of from about 50 to about 150° C. to convert the MW 132 cyclic acetal to more volatile cyclic acetals and/or other degradation products, and
e) separating the more volatile cyclic acetals and/or other degradation products from the 1,3-propanediol by distillation or gas stripping.

In the most preferred embodiment of this invention, steps d) and e) are carried out together (such as in the same vessel or column) such that the volatile cyclic acetals and/or other degradation products are separated from the 1,3-propanediol as they are formed. In another embodiment, an acidic zeolite can be used in place of the cationic acid exchange resin. In such case, the temperature preferably is from about 80 to about 200° C.

DETAILED DESCRIPTION OF THE INVENTION

The 3-hydroxypropanal (HPA) aqueous solution which is the starting material of the present invention, can be produced by a number of different processes. The aforementioned U.S. Pat. Nos. 4,873,378, 4,873,379, 5,053,562, 5,030,766, 5,210,318, 5,256,827, 5,304,686, and 5,304,691, all of which are herein incorporated by reference, describe different methods for producing aqueous solutions of HPA. HPA can also be produced by hydration of acrolein in the presence of acidic catalysts. Processes for accomplishing this result are described in U.S. Pat. Nos. 5,426,249, 5,015, 789, 5,171,898, 5,276,201, 5,334,778, and 5,364,987, all of which are herein incorporated by reference.

A preferred method for carrying out the entire process of the present invention is described in U.S. Pat. No. 5,786,524, which is herein incorporated by reference, and is generally as follows. EO is hydroformylated in a reactor such as a bubble column or agitated tank at about 200 to about 5000 psi (about 1380 to about 34,500 kPa) of syngas having a ratio of hydrogen to carbon monoxide of about 1:5 to about 25:1 at about 50 to about 110° C. in the presence of a hydroformylation catalyst at a concentration of about 0.05 to about 15 weight percent, preferably about 0.05 to about 1 percent.

The hydroformylation reaction effluent is extracted with a small amount of water at water-solvent ratios ranging from about 2:1 to about 1:20 at about 5 to 55° C. under an atmosphere of greater than about 50 psi (350 kPa) carbon monoxide. The solvent layer containing more than about 90 percent of the catalyst in active form is recycled back to the hydroformylation reactor. The HPA is thereby concentrated in the water phase at about 10 to about 45 weight percent.

The catalyst may be removed from this aqueous solution of HPA by any known means including first oxidizing the catalyst and then extracting it utilizing an acid ion exchange resin. The ion exchange resin may be a weak (carboxylic) or strong (sulfonic) acid cation exchange resin. Examples include AMBERLYST® 15 or 35, XN-1010, AMBERLITE® IR-118, IR120, IRC76, IRC50, A1200; DOWEX® 50, M31, CCR2, plus BIO RAD® AG50W-X2, AMBERSEP® 252H, and Purolite® C-100 resins.

After neutralization of the aqueous solution of 3-hydroxypropanal, the aqueous solution is hydrogenated. This may be carried out by hydrogenation over a fixed bed of hydrogenation catalyst at typically about 100 to about 2000 psi (about 690 to about 13,800 kPa) of hydrogen. The hydrogenation catalyst can be any of those described in U.S. Pat. No. 5,786,524, which is herein incorporated by reference, including catalysts of a group VIII metal such as nickel, cobalt, ruthenium,platinum, or palladium. Initial hydrogenation is conducted at about 40 to about 80° C. and the temperature is increased to about 120 to about 175° C. to encourage the reaction of reactive components such as cyclic acetals to revert back to PDO. Finally, water and entrained light (low boiling) solvent and highly volatile (low boiling) impurities are distilled from the crude PDO. The dried crude product stream containing MW132 acetal and PDO is treated as described below to recover PDO in high yield and high purity.

Crude PDO as described above can exhibit high levels of MW 132 cyclic acetal impurity. This impurity is undesirable and limits PDO recovery efficiencies during subsequent distillation. It can form by reaction of PDO with HPA.

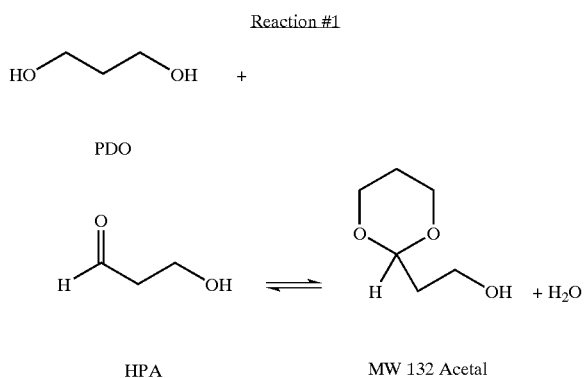

Reaction #1

PDO

HPA

MW 132 Acetal

The 2-ethylene-1,3-dioxane cyclic acetal (EDCA) formed upon acid catalyzed decomposition of MW 132 acetal is known to be much more volatile than PDO. The following formula explains the dehydration of MW 132 acetal to form the 2-ethylene-1,3-dioxane cyclic acetal (EDCA) that can be readily separated from the PDO by distillation. Acidic zeolites and acid form cationic exchange resins (such as used for cobalt removal) can be used to purify PDO via reaction of MW 132 acetal to form EDCA:

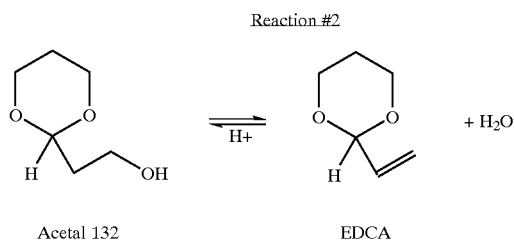

Reaction #2

Acetal 132

EDCA

Thus, the dried crude PDO stream containing the undesirable MW 132 cyclic acetal is contacted with an acid form cationic exchange resin or an acidic zeolite under conditions which favor the reaction scheme shown above for the conversion of MW 132 acetal to EDCA. This step is combined with removal of the EDCA via concerted distillation or via use of a stripping gas such as nitrogen or steam.

Concerted distillation and reaction, where distillation and reaction are combined in the same processing unit to separate reactants from products as they are formed, may employ any of the well known methods for conducting a "reactive distillation." Alternatively, an inert gas such as nitrogen may be used to strip the reaction mixtures (concerted stripping and reaction) of the more volatile degradation product of MW132 acetal (EDCA), and thus prevent reformation of MW132 via chemical equilibrium. Use of water vapor (steam) is a common commercial practice for providing process heat and an inert stripping gas. In this case, the stripping is again conducted in the same processing unit as the reaction of MW132 acetal. The reaction products are removed as formed in order to drive the chemical equilibrium to eliminate or reduce the presence of MW132 acetal. In this manner, the combination of acid-catalyzed reaction plus stripping in the same processing step effects reactant-product separation in the same manner as the "reactive distillation" combination of acid-catalyzed reaction and distillation.

In general, water was found to suppress the reversion of and removal of MW132 acetal. However, small amounts of water are generally present due to incomplete removal, sorption in the solid catalyst, or due to the dehydration reaction itself (#1 above) and may allow a portion of the MW132 removal to proceed via the reversal of reaction #1. HPA, if formed in this manner, may then be further dehydrated to highly volatile acrolein, which is readily stripped or distilled from the reaction mixture. Regardless of which mechanism dominates, the concerted acid-catalyzed reaction with separation (distillation or stripping) of volatile reaction products results in a reduction in the MW132 impurity of the product PDO. Concerted distillation or inert gas stripping is required to drive the chemical equilibrium away from the thermodynamically favored MW132 cyclic acetal. An acid formed zeolite can also be used during the procedure described above to catalyze the degradation of the MW132 acetal.

Use of the acid form cationic exchange resin with concerted separation produces virtually complete conversion of the MW 132 acetal. The reaction is preferably carried out at a temperature of from about 50 to about 150° C., more preferably at from about 80 to about 120° C. Contacting with the resin catalyst is either conducted batchwise, or in a continuous column, using well known reactor design methods to insure virtually complete conversion of the MW132 acetal. Batchwise contacting at about 80 to about 120° C. may be conducted for about 1 to about 5 hours with about 10 weight percent of acid resin, for example, to effect complete conversion. Alternately, the contacting may be effected in a continuous reaction vessel, preferably a column, with a "weight hourly space velocity" (weight of impure PDO feed per weight of acid resin per hour-"WHSV") of about 0.1 to 1 per hour.

With zeolites, the activity for acetal reversion is lower, such that a higher temperature or increased contact time with the zeolite is required. The reaction with acidic zeolite is preferably carried out at a temperature of from about 70 to about 250° C.,more preferably at from about 90 to about 170° C., via batch or continuous contacting. Similar contacting times or weight hourly space velocities could be used. For either system, the combination of temperature and contact time with the solid acidic purifier (acid form cationic exchange resin or acidic zeolite) must be optimized to limit the production of undesirable color-imparting impurities and to minimize the production of dimer and higher oligomers of PDO.

The preferred catalysts are ion exchange resins with strongly acidic cation exchange (acid form cationic exchange resins). These include the gel type or macroreticular (macroporous) ion exchange resins with sulfonic acid functional groups wherein the sulfonic acid function is bonded directly or indirectly to an organic polymer backbone. Examples include Rohm and Haas Amberlite® or Amberlyst® A200, A252, IR-118, IR120, A15, A35, XN-1010, or uniform particle size A1200 resins; Dow MSC-1, M-31, or Dowex® 50-series resins, Sybron® C-249, C-267, CFP-110 resins; Purolite® C-100 or C-150 resins; Resintech® CG8; IWT C-211, SACMP; IWT C-381; or other comparable commercial strong acid cation exchange resins. Another example of cation exchange resins is NAFION® acidified perfluorinated polymer of sulphonic acid.

The suitable zeolite catalysts contain one or more modified zeolites preferably in the acidic form. These zeolites should contain pore dimensions large enough to admit the entry of the acyclic or aliphatic compounds. The preferred zeolites include, for example, zeolites of the structural types MFI (e.g., ZSM-5), MEL(e.g., ZSM-11), FER (e.g., ferrierite and ZSM-35), FAU (e.g., zeolite Y), BEA (e.g., beta), MFS (e.g., ZSM-57), NES (e.g. NU-87), MOR (e.g. mordenite), CHA (e.g., chabazite), MTT (e.g., ZSM-23), MWW (e.g., MCM-22 and SSZ-25), EUO (e.g. EU-1, ZSM-50, and TPZ-3), OFF (e.g., offretite), MTW (e.g., ZSM-12) and zeolites ITQ-1, ITQ-2, MCM-56, MCM-49, ZSM-48, SSZ-35, SSZ-39 and zeolites of the mixed crystalline phases such as, for example, zeolite PSH-3. The structural types and references to the synthesis of the various zeolites can be found in the "Atlas of Zeolite Structure Types" (published on behalf of the Structure Commission of the International Zeolite Association), by W. M. Meier, D. H. Olson and Ch. Baerlocher, published by Butterworth-Heinemann, fourth revised edition, 1996. Structural types and references to the zeolites mentioned above are available on the World Wide Web at www.iza-structure.org Such zeolites are commercially available from Zeolyst International, Inc. and ExxonMobil Corporation. Additional examples of suitable zeolite catalysts can be found in U.S. Pat. Nos. 5,762,777; 5,808,167; 5,110,995; 5,874,646; 4,826,667; 4,439,409; 4,954,325; 5,236,575; 5,362,697; 5,827,491; 5,958,370; 4,016,245; 4,251,499; 4,795,623; 4,942,027 and WO99/35087, which are hereby incorporated by reference.

EXAMPLES

Example 1 (Comparative)

Acid Resin Treatment Prior to Distillation

This experiment entailed treatment of 1500 grams of crude PDO following water removal, via distillation, with 43.5 grams dry A15 (Amberlyst® A15 resin) strong acid form cationic exchange resin under a nitrogen atmosphere for 3 hours at 100° C. with minimal separation (stripping). The treated material was bright yellow. MW 132 acetal was reduced only from 3.2 wt % to 2.6 wt %. The treated material was distilled and successive distillation cuts showed reduction in MW 132 acetal from 11% to 2 wt % but formation of up to 2700 ppm acrylate by the final cut. Excessive formation of acrylate can be expected because of the strong acid treatment which freed 3-hydroxypropionic acid, thus giving maximal ester and ultimately acrylate formation. This example illustrates that no significant MW132 acetal removal was observed for the resin treatment in the absence of concerted separation (stripping or distillation) of the volatile impurities.

Example 2

Acid Resin Treatment with Concerted Stripping to Remove Acetal

The results of this experiment are shown in Table 1. 1 gram of vacuum dried A15 strong acid resin was added to 10 grams of the PDO distillate containing 1.38 wt % MW 132 cyclic acetal from which a majority of the water had been removed by distillation. The sample was heated via a metal block heater to 100° C. with vigorous nitrogen stripping (concerted stripping) as evidenced by an expansion of the liquid by about 10 volume percent. MW 132 acetal was readily eliminated with formation of significant quantities of di- and tri-PDO via direct PDO self condensation.

TABLE 1

| Sample | Time Hours | MW 132 Acetal wt % | di-PDO wt % | tri-PDO wt % |
|---|---|---|---|---|
| 167-9 | 0 | 1.38 | 0 | 0 |
| 194-1 | 1 | 0.345 | 0.548 | 1.356 |
| 194-2 | 3 | 0.017 | 3.009 | 1.934 |
| 194-3 | 5 | 0.012 | 6.667 | 1.997 |

This study was repeated with a different distillate. 1 gram of dry A15 resin was used to treat 12 grams of PDO distillate. The MW 176 (a higher boiling cyclic acetal) and MW 132 acetals were eliminated. Di- and tri-PDO formed in significant quantities. The results are shown in Table 2.

TABLE 2

| | Resin Dry Stripping | | | | | |
|---|---|---|---|---|---|---|
| Sample | Time Hours | EG wt % | $rt^1$ = 21.69 Acrylate[2] wt % | MW 132 Acetal wt % | MW 176 rt = 26.18 wt % | $rt^1$ = 24.6 di-PDO wt % | $rt^1$ = 29.4 tri-PDO wt % |
| High acetal feed | | | | | | | |
| 197-3 | 0 | 0.142 | 0.416 | 2.409 | 0.421 | 0 | 0 |
| 20b | 1 | 0.126 | 0.175 | 1.032 | 0 | 0.615 | 2.559 |
| 20d | 2 | 0.122 | 0.078 | 0.282 | 0 | 3.004 | 3.938 |
| 20f | 5 | 0.084 | 0.031 | 0.067 | 0 | 5.929 | 3.535 |
| Low acetal feed | | | | | | | |
| 192-5 | 0 | 0 | 0.023 | 0.3 | 0.051 | 0 | 0 |
| 20a | 1 | 0 | 0 | 0.077 | 0 | 0.557 | 0.138 |

TABLE 2-continued

| | | | Resin Dry Stripping | | | | |
| Sample | Time Hours | EG wt % | rt[1] = 21.69 Acrylate[2] wt % | MW 132 Acetal wt % | MW 176 rt = 26.18 wt % | rt[1] = 24.6 di-PDO wt % | rt[1] = 29.4 tri-PDO wt % |
| --- | --- | --- | --- | --- | --- | --- | --- |
| 20c | 2 | 0 | 0 | 0.044 | 0 | 2.027 | 0.156 |
| 20e | 5 | 0 | 0 | 0.028 | 0 | 4.486 | 0.206 |

[1]rt is chromatographic retention time.
[2]3-hydroxypropylacrylate

Another similar experiment was carried out using 5 wt % of M31 strong acid form cationic exchange resin (macroreticular resin). As in the previous experiments, the amount of the MW 132 acetal was decreased and PDO dimer was produced with contacting with acid catalyst and with concerted nitrogen stripping. The results are shown in Table 3.

TABLE 3

| | Acid Resin + N2 Strip | | |
| 5% resin 100° C. Catalyst | Time Hours | MW 132 Acetal wt % | di-PDO wt % |
| --- | --- | --- | --- |
| none | 12 | 2.865 | 0 |
| A15 | 12 | 1.509 | 10.427 |
| M31 | 12 | 1.024 | 10.316 |

Example 3

Acid Resin Dry Stripping with Subsequent Redistillation

A twice distilled PDO product sample exhibiting a visible light yellow color upon testing for color body precursors was contacted with 5 wt % dry A15 strong acid form cationic exchange resin with nitrogen stripping for 4 hours at 105° C. MW 132 acetal was virtually eliminated while 1.7 wt % di-PDO was formed (Table 4), giving a gc (gas chromatographic) purity of 97.9 wt %. The treated sample was redistilled at 9 mm Hg (1.3 kPa) in a small 2-ft (0.6 meter) concentric tube column with a bottoms temperature of 121 to 123° C. Distillation showed ready separation of di-PDO from the PDO distillate. Distillate cuts were substantially reduced in MW 132 acetal with the gc purity approaching 99.9%. The color test now gave only slightly yellow tint, indicating a reduction in the amount of color body precursors.

TABLE 4

| | Acid Stripping With Redistillation | | | |
| | | grams | MW 132 ppm | PDO wt % | di-PDO wt % |
| --- | --- | --- | --- | --- | --- |
| Feed | | 160.44 | n.d. | 97.933 | 1.713 |
| Dist cut# | 1 | 17.34 | 500 | 99.766 | 0 |
| | 2 | 43.15 | 200 | 99.910 | 0 |
| | 3 | 51.19 | 0 | 99.894 | 0 |
| | 4 | 43.41 | 0 | 99.846 | 0 |
| | Total | 155.09 | | | |

A less pure sample containing 3 wt % MW 132 acetal, which exhibited significant color when analyzed for color body precursors, was similarly treated with 5 wt % strong acid resin (A15) while nitrogen stripping. The resulting PDO contained no MW 132 acetal after 4 hours, but it did contain 2.9 wt % di-PDO. Redistillation at 8 mm Hg (1.3 kPa) and 122 to 129° C. bottoms temperature in a 2-foot (0.6 meter) concentric tube column gave the distillation cuts shown in Table 5. Again, the acid resin stripping eliminated a significant portion of the MW 132 acetal such that distillation overhead products free of this impurity could then be produced. Di-PDO formed during the resin treatment was readily separated by distillation. The purities of the final distillate cuts would have been quite high if not for progressive formation of MW 102 acetal (2-methyl-1,3-dioxane), which is known to be more volatile than PDO, during the distillation. Yet another distillation would have rid the product of this impurity.

TABLE 5

| | Acid Stripping With Redistillation | | | | |
| | | grams | MW 132 ppm | PDO wt % | di-PDO wt % | 2-me-dioxan MW 102 Acetal wt % |
| --- | --- | --- | --- | --- | --- | --- |
| Feed | | 192.66 | n.d. | 95.204 | 2.974 | 0 |
| Dist cut# | 1 | 15.96 | 460 | 99.756 | 0 | 0.304 |
| | 2 | 50.45 | 0 | 98.292 | 0 | 0.308 |
| | 3 | 45.87 | 0 | 99.106 | 0 | 0.505 |
| | 4 | 52.60 | 0 | 99.329 | 0 | 0.606 |
| | 5 | 10.57 | 0 | 98.579 | 0 | 1.186 |
| | Total | 175.45 | | | | |

Example 4

Inorganic solid acids such as silica-aluminas or zeolites are more amenable to commercial use in a nitrogen or steam stripper. However, their activity in dehydrating beta-hydroxy cyclic acetals such as MW 132 is poorer than the activity strong acid ion exchange resins under comparable conditions (Table 6). The highly active resins, on the other hand, make more di- and tri-PDO as byproducts. These oligomers are not believed to be color precursors, however, and are more readily separated by distillation than the original MW132 acetal. Temperatures and reaction (contacting) times preferably are optimally adjusted for the acid form cationic exchange resin vs. the acidic zeolite to maximize MW132 acetal reversion to PDO while minimizing the formation of other heavy impurities.

TABLE 6

Inorganic Solid Acids vs. Ion Exchange Resin for Acid Stripping

| Solid Acid | Type | Temp °C. | Solid Acid wt % | Time Hours | MW 132 Initial wt % | MW 132 Final wt % | di-PDO Final wt % |
|---|---|---|---|---|---|---|---|
| ASA | Amorphous silica-alumina | 100 | 23 | 3 | 0.296 | 0.253 | 0 |
| ASA | Amorphous silica-alumina | 155 | 22 | 2 | 0.296 | 0.209 | 0 |
| Y | H+ zeolite | 100 | 5.7 | 1 | 0.296 | 0.323 | 0 |
| ZSM5 | H+ zeolite | 100 | 4 | 3 | 2.4 | 1.5 | 0 |
| ZSM5 | H+ zeolite | 100 | 4 | 3 | 0.3 | 0.07 | 0 |
| A15 | Strong acid ion exchange resin | 105 | 5 | 4 | 0.058 | 0 | 1.73 |
| A15 | Strong acid ion exchange resin | 105 | 5.2 | 4 | 3 | 0 | 2.97 |
| A15 | Strong acid ion exchange resin | 105 | 5 | 12 | 2.9 | 1.5 | 10.3 |
| A15 | Strong acid ion exchange resin | 100 | 10 | 3 | 1.38 | 0.017 | 3 |

We claim:

1. A process for producing 1,3-propanediol comprising the steps of:
   a) forming an aqueous solution of 3-hydroxypropanal,
   b) hydrogenating the 3-hydroxypropanal to form a first crude 1,3-propanediol mixture comprising 1,3-propanediol, water, and MW 132 cyclic acetal,
   c) distilling the first crude 1,3-propanediol mixture to remove water and low boiling impurities and form a second crude 1,3-propanediol mixture,
   d) contacting the second crude 1,3-propanediol mixture with an acid form cationic exchange resin at a temperature of from about 50 to about 150° C. to convert the MW 132 cyclic acetal to more volatile cyclic acetals and/or other degradation products, and
   e) separating the more volatile cyclic acetals and/or other degradation products from the 1,3-propanediol by distillation or gas stripping.

2. The process of claim 1 wherein steps d) and e) are carried out together such that the volatile cyclic acetals and/or other degradation products are separated from the 1,3-propanediol as they are formed.

3. The process of claim 1 wherein the temperature in step d) is from about 80 to about 120° C.

4. The process of claim 1 wherein the second crude 1,3-propanediol mixture is contacted with the cationic exchange resin batchwise for from about 1 to about 5 hours.

5. The process of claim 1 wherein the second crude 1,3-propanediol mixture is contacted with the cationic exchange resin in a continuous reaction vessel at a weight hourly space velocity of about 0.1 to about 10.

6. The process of claim 1 comprising the further step of distilling the 1,3-propanediol to separate 1,3-propanediol from high boiling impurities formed as a result of step d).

7. A process for producing 1,3-propanediol comprising the steps of:
   a) forming an aqueous solution of 3-hydroxypropanal,
   b) hydrogenating the 3-hydroxypropanal to form a first crude 1,3-propanediol mixture comprising 1,3-propanediol, water, and MW 132 cyclic acetal,
   c) distilling the first crude 1,3-propanediol mixture to remove water and low boiling impurities and form a second crude 1,3-propanediol mixture,
   d) contacting the second crude 1,3-propanediol mixture with an acidic zeolite at a temperature of from about 70 to about 250° C. to convert the MW 132 cyclic acetal to more volatile cyclic acetals and/or other degradation products, and
   e) separating the more volatile cyclic acetals and/or other degradation products from the 1,3-propanediol by distillation or gas stripping.

8. The process of claim 7 wherein steps d) and e) are carried out together such that the volatile cyclic acetals and/or other degradation products are separated from the 1,3-propanediol as they are formed.

9. The process of claim 7 wherein the temperature in step d) is from about 90 to about 170° C.

10. The process of claim 7 wherein the second crude 1,3-propanediol mixture is contacted with the zeolite batchwise for from about 1 to about 5 hours.

11. The process of claim 7 wherein the second crude 1,3-propanediol mixture is contacted with the zeolite in a continuous reaction vessel at a weight hourly space velocity of about 0.1 to about 10.

12. The process of claim 7 comprising the further step of distilling the 1,3-propanediol to separate 1,3-propanediol from high boiling impurities formed as a result of step d).

* * * * *